US006472567B2

(12) United States Patent
Ishikawa et al.

(10) Patent No.: US 6,472,567 B2
(45) Date of Patent: *Oct. 29, 2002

(54) PROCESS FOR THE PRODUCTION OF STYRENE COMPOUND, AND STYRENE COMPOUND FREE FROM BIPHENYL

(75) Inventors: Shin-ichi Ishikawa, Yamaguchi (JP); Hisao Eguchi, Yamaguchi (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/923,347

(22) Filed: Aug. 8, 2001

(65) Prior Publication Data

US 2002/0026084 A1 Feb. 28, 2002

Related U.S. Application Data

(63) Continuation-in-part of application No. 09/238,585, filed on Jan. 28, 1999.

(30) Foreign Application Priority Data

Jan. 30, 1998 (JP) ............................................. 10-18681
Jun. 12, 1998 (JP) ........................................... 10-165389
Jul. 24, 1998 (JP) ........................................... 10-209488
Jul. 24, 1998 (JP) ........................................... 10-209489

(51) Int. Cl.$^7$ ............................................. C07C 41/06
(52) U.S. Cl. ...................... 568/658; 568/628
(58) Field of Search .................... 568/628, 658

(56) References Cited

U.S. PATENT DOCUMENTS 4,143,221 A  3/1979  Naarmann et al.
4,293,497 A  * 10/1981  Cardenas et al. ............ 549/410

FOREIGN PATENT DOCUMENTS

JP  60072833  4/1985
JP  1106835  4/1989
JP  2160739  6/1990
JP  2000-23912 A  9/2000

OTHER PUBLICATIONS

Tamura et al., Journal of the American Chemical Society, vol. 93:6, Mar. 1971, pp. 1487–1489.*
Felkin et al., Tetrahedron, vol. 31, No. 22, Nov. 1975, pp. 2735–2748.*
Nunomoto et al., Fujiyama Kogyo Koto Senmonn Kakko Kiyo No. 20, 1986, English translation pp. 1–9.*
Tamura et al., Synthesis–International Journal of Methods in Synthetic Organic Chemistry, No. 6, Jun. 1971, pp. 303–305.*
"Termination of Transfer Reactions in Cationic Polymerization of Styrene by Friedel–Crafts Catalysts", Journal of Polymer Science, vol. XXXIII, Issue No. 126, (1958, No Month Provided), pp. 496–500.

"Cationic Copolymerization of Trioxane with Styrene", Die Macromolekulare Chemie, vol. 1991, (1968, No Month Provided), pp. 96–103.

Cationic Polymerization, pp. 23–24, Table 2.6 and 2.7 (Kagaku Dojin, 1971, No Month Provided) Discloses that Various Lewis Catalysts Including FeCl$_3$ are Effective as the Polymerization Initiator in Cationic Polymerization of Various Monomers.

Koehi Tamao et al, "Nickel–Phosphine Complex–Catalyzed Grignard Coupling. I. Cross–Coupling of Alkyl, Aryl, and Alkenyl Grignard Reagents with Aryl and Alkenyl Halides: General Scope and Limitations" Bulletin of the Chemical Society of Japan, vol. 49 (7) 1958–1969 (1976, No Month Provided).

Stephen M. Neumann et al, "Synthesis of Olefins. Cross Coupling of Alkenyl Halides and Grignard Reagents Catalyzed by Iron Complexes", J. Org. Chem., vol. 40. No. 5, 1975, No Month Provided, pp. 599–606.

The Chemistry of Cationic Polymerization (Pergamon Press, 1963, No Month Provided), pp. 238–239. P.H. Plesch.

Edward G. Paul et al, "Reaction of 2,3,4,6–Tetramethoxybenzaldehyde with Aluminum Chloride. Selective Cleavage at Position 2 and Selective Ether Exchange at Position 3", J. Or. Chem. vol. 44, No. 13, 1979, No Month Provided, pp. 2307–2308.

The Chemistry of Ether Linkage (John Wiley & Sons, 1967, No Month Provided), p. 53 "IV. Cleavage by Metal Halides" Saul Patai.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

A process for the production of a styrene compound is provided. The process comprises reacting a Grignard reagent prepared from a tertiary butoxyphenyl halide with a vinyl halide in the presence of a catalyst, wherein the catalyst is at least one member selected from the group consisting of manganese catalyst, iron catalyst, cobalt catalyst and rhodium catalyst. The process overcomes the problems involved in the prior art, and is economical and safe. The styrene compound by the process is free from biphenyl.

14 Claims, No Drawings

PROCESS FOR THE PRODUCTION OF STYRENE COMPOUND, AND STYRENE COMPOUND FREE FROM BIPHENYL

CROSS-REFERENCE TO THE RELATED APPLICATION

This application is a continuation-in-part application of application Ser. No. 09/238,585, filed Jan. 28, 1999, entitled "PROCESS FOR THE PRODUCTION OF STYRENE DERIVATIVE", now pending.

FIELD OF THE INVENTION

The present invention relates to a process for the production of a styrene compound, and a styrene compound free from biphenyl. More particularly, the present invention relates to a process for the production of a styrene compound which comprises reacting a Grignard reagent prepared from an aromatic halogen compound with a vinyl halide in the presence of a catalyst, and styrene compound free from biphenyl.

BACKGROUND OF THE INVENTION

A styrene derivative towards which the present invention is directed is very useful as a raw material of functional high molecular compounds, medicines, agricultural chemicals, etc. For example, para-tertiary butoxystyrene (hereinafter referred to as "PTBS") is known to be extremely useful as a raw material of a resist for use in super LSI's, etc. (JP-A-59-199705 (The term "JP-A" as used herein means an "unexamined published Japanese patent application"), JP-A-3-277608). Further, meta-tertiary butoxystyrene (hereinafter referred to as "MTBS") is known to be useful as an intermediate raw material of functional high molecular compounds, medicines, agricultural chemicals, etc. (JP-A-2-160739).

Two processes for the production of a styrene derivative such as PTBS and MTBS have been heretofore known.

U.S. Pat. No. 4,603,101 and JP-A-59-199705 disclose a process involving the reaction of a Grignard reagent prepared from halostyrene with perbenzoic acid tertiary butyl ester. However, this production process gives a low reaction yield. In addition, this production process is disadvantageous in that it requires the use of a perbenzoic acid tertiary butyl ester, which is difficult to be available in a large amount and is explosive. Thus, this production process leaves something to be desired in mass production of a styrene derivative such as PTBS and MTBS.

On the other hand, JP-B-4-71896 (The term "JP-A" as used herein means an "unexamined published Japanese patent application") and JP-A-2-160739 disclose a process involving the reaction of a Grignard reagent prepared from a tertiary butoxyphenyl halide with a vinyl halide in the presence of a nickel-phosphine complex catalyst. However, this production process is disadvantageous in that it requires the use of a nickel-phosphine complex catalyst which is expensive and very toxic, although providing some improvement in reaction yield. The above cited patent applications describe that bidentate phosphine complexes such as dichloro[1, 2-bis (diphenylphosphino)ethane]nickel and dichloro[1, 3-bis (diphenylphosphino)propane] nickel are effective for the progress of this reaction in a high yield. However, these catalysts are expensive and very toxic. Accordingly, even if this production process is used, it is difficult to produce a styrene derivative such as PTBS and MTBS economically and safely. Thus, this production process, too, leaves something to be desired in mass production of a styrene derivative such as PTBS and MTBS.

Further, the present inventors have found that in the case of producing tertiary-butoxystyrene by those processes, biphenyl is produced as a reaction by-product. Biphenyl has the characteristic of having strong absorption to far ultraviolet light of excimer laser or the like used in super LSI. For this reason, if biphenyl is present in a resist resin, there are the problems that the presence decreases light permeability and also decreases resolution of a resist, thus inducing unfavorable trouble. In other words, it is preferable for tertiary-butoxystyrene used in resist to not contain biphenyl as an impurity. However, boiling points of tertiary-butoxystyrene and biphenyl are very close, and thus it is extremely difficult to remove biphenyl once produced, by general distillation operation.

SUMMARY OF THE INVENTION

It is therefore an object of the present invention to provide a process for the production of a styrene compound giving improvements over the prior art, and a styrene compound free from biphenyl. More particularly, the object of the present invention is to provide a process for the production of a styrene compound such as PTBS and MTBS which gives solution to the prior art problems and hence provides excellent economy and safety, and also provide a high quality tertiary butoxystyrene free from biphenyl.

The above object of the present invention will become more apparent from the following detailed description and examples.

The inventors made extensive studies of solution to the prior art problems. As a result, it was found that the use of a specific catalyst in a process for the production of a styrene compound such as PTBS and MTBS involving the reaction of a Grignard reagent prepared from tertiary butoxyphenyl halide with a vinyl halide in the presence of a catalyst makes it possible to produce such a styrene compound economically and safely on an industrial basis. It was further found that using this catalytic process makes it possible to achieve a reaction which does not form biphenyl by-product at all. Thus, the present invention has been worked out.

That is, the present invention provides a process for the production of a styrene compound which comprises reacting a Grignard reagent prepared from a tertiary butoxyphenyl halide represented by the following formula (I):

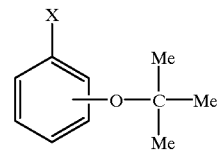

wherein X represents a halogen atom, with a vinyl halide in the presence of a catalyst, wherein said catalyst is at least one member selected from the group consisting of a manganese catalyst, an iron catalyst, a cobalt catalyst and a rhodium catalyst.

The present invention also provides a styrene compound free from biphenyl, obtained using this process.

DETAILED DESCRIPTION OF THE INVENTION

The present invention will be further described with reference to the production of PTBS.

The Grignard reagent to be used in the production process of the present invention is not specifically limited so far as it is prepared from an aromatic halogen compound. Thus, the Grignard reagent of the present invention can be easily prepared by any ordinary method. In other words, the Grignard reagent of the present invention can be easily prepared, e.g., by a process which comprises the reaction of metallic magnesium with para-tertiary butoxyphenyl halide in a solvent. If activated metallic magnesium is used in this preparation process, particularly good results can be given. Examples of effective methods for activating metallic magnesium include a method involving heating of a suspension of metallic magnesium in a solvent with stirring and a method involving stirring of such a suspension mixed with a slight amount of iodine, iodide such as methyl iodide, bromide such as dibromoethane or the like.

In accordance with the production process of the present invention, the reaction of a Grignard reagent prepared by the above method with a vinyl halide in the presence of one or more catalysts selected from the group consisting of manganese catalyst, iron catalyst, cobalt catalyst and rhodium catalyst makes it possible to produce PTBS safely in a high yield at a low cost.

Examples of the vinyl halide used in the production process of the present invention include vinyl fluoride, vinyl chloride, vinyl bromide, and vinyl iodide. These vinyl halides may be used singly or in admixture. In general, vinyl chloride gas and/or vinyl bromide gas are selected taking into account the economy and availability.

The catalyst used herein comprises one or more catalysts selected from the group consisting of manganese catalyst, iron catalyst, cobalt catalyst and rhodium catalyst.

The term "manganese catalyst" as used herein means to indicate a catalyst comprising manganese element as an effective component. Thus, the manganese catalyst used herein is not specifically limited. In practice, however, manganese powder, manganese compounds such as manganese chloride (II), manganese bromide (II), manganese iodide (II), manganese fluoride (II), manganese acetate (II), manganese acetate (III), manganese formate (II), manganese oxalate (II), manganese benzoate (II), manganese stearate (II), manganese borate (II), manganese acetylacetonate (II), manganese acetylacetonate (III), manganese carbonate (II), manganese sulfate (II), manganese nitrate (II) and manganese phosphate (II), hydrates thereof, various complex catalysts derived from these compounds, etc. may be used.

The term "iron catalyst" as used herein means to indicate a catalyst comprising iron element as an effective component. Thus, the iron catalyst used herein is not specifically limited. In practice, however, ferrous halide, ferric halide, catalyst prepared from ferrous halide, catalyst prepared from ferric halide, etc. may be used.

The term "catalyst prepared from ferrous halide" as used herein means to indicate a catalyst derived from ferrous halide or a catalyst comprising ferrous halide as an effective component. Examples of such a catalyst include hydrates and various complex catalysts of ferrous halide.

The term "catalyst prepared from ferric halide" as used herein can be similarly defined. Examples of such a catalyst include hydrates and various complex catalysts of ferric halide.

Specific examples of the iron catalyst used in the production process of the present invention include iron powder, iron compounds such as ferrous chloride (II), ferric chloride (III), ferrous bromide (II), ferric bromide (III), ferrous iodide (II), ferrous fluoride (II), ferric fluoride (III), ferrous acetate (II), ferrous oxalate (II), ferric oxalate (III), ferric citrate (III), ferric perchlorate (III), ferric acetylacetonate (III), ferric nitrate (III), ferric phosphate (III), ferrous sulfate (II) and ferrous sulfate (II), hydrates thereof, and various complex catalysts derived from these compounds.

The term "cobalt catalyst" as used herein means to indicate a catalyst comprising cobalt element as an effective component. Thus, the cobalt catalyst used herein is not specifically limited. In practice, however, cobalt powder, cobalt compounds such as cobalt chloride (II), cobalt bromide (II), cobalt iodide (II), cobalt fluoride (II), cobalt acetate (II), cobalt acetate (III), cobalt formate (II), cobalt oxalate (II), cobalt benzoate (II), cobalt stearate (II), cobalt borate (II), cobalt acetylacetonate (II), cobalt acetylacetonate (III), cobalt carbonate (II), cobalt sulfate (II), cobalt nitrate (II) and cobalt phosphate (II), hydrates thereof, various complex catalysts derived from these compounds, etc. may be used.

The term "rhodium catalyst" as used herein means to indicate a catalyst comprising rhodium element as an effective component. Thus, the rhodium catalyst used herein is not specifically limited. In practice, however, rhodium powder, rhodium compounds such as rhodium-carbon, rhodium chloride (II), rhodium bromide (II), rhodium acetate (II), rhodium acetate (III), rhodium acetylacetonate (II) and rhodium acetylacetonate (III), hydrates thereof, various complex catalysts derived from these compounds, etc. may be used.

In the production process of the present invention, the above catalysts may be used singly or in admixture. If one or more catalysts selected from the group consisting of manganese halide, manganese acetate, iron halide, iron acetate, cobalt halide, cobalt acetate, rhodium halide and rhodium acetate are used, particularly good results (high yield) can be given. The amount of the catalyst to be used in the production process of the present invention is not specifically limited. In general, however, it is from about $10^{-4}$ to $10^1$ mols per mole of the Grignard reagent used.

The foregoing prior art production process (as disclosed in JP-B-4-71896) is disadvantageous in that it requires the use of a nickel-phosphine complex catalyst which is expensive and very toxic. Further, this production process has the problem that biphenyl which is unfavorable impurity is by-produced, and thus was not satisfactory as and industrial production of PTBS. The inventors found for the first time that one or more catalysts selected from the group consisting of manganese catalyst, iron catalyst, cobalt catalyst and rhodium catalyst, which are inexpensive and safe, are effective for the reaction of a Grignard reagent prepared from para-tertiary butoxyphenyl halide with a vinyl halide. Among these catalysts, one or more catalysts selected from the group consisting of manganese halide, manganese acetate, iron halide, iron acetate, cobalt halide, cobalt acetate, rhodium acetate are very inexpensive and safe catalysts. The production process of the present invention using such a catalyst is extremely useful for the industrial production of PTBS.

The production process of the present invention is normally effected in a solvent in the presence of an inert gas atmosphere such as nitrogen and argon. Examples of the reaction solvent used in the production process of the present invention include ether solvent, oxygen-containing solvent, nitrogen-containing solvent, aromatic hydrocarbon solvent, and aliphatic hydrocarbon solvent. In general, these solvents may be used singly or in admixture. In particular, if tetrahydrofuran or a mixed solvent containing tetrahydrofuran is used, good results (high yield) can be given. The production process of the present invention is normally effected at a temperature of from 0° C. to the reflux temperature of the solvent used.

After completion of the reaction, the reaction solution is treated with an acidic aqueous solution by an ordinary method to cause the separation of an organic phase. Subsequently, the organic phase is rinsed, and then subjected to distillation to remove the solvent therefrom. A polymerization inhibitor such as tertiary butyl catechol is added to the reaction solution which is then subjected to distillation to obtain desired PTBS.

The production process of the present invention is not limited to the above production of PTBS but can find wide application in the same reaction for the production of styrene derivatives from aromatic halogen compounds. If applied to the production of a tertiary butoxystyrene such as PTBS and MTBS, the production process of the present invention can provide particularly good results (high yield).

The term "aromatic halogen compound" as used herein is a general term for compounds substituted by halogen at least one position in aromatic ring.

The aromatic halogen compound used in the present invention is preferably a tertiary butoxyphenyl halide represented by the following formula (I):

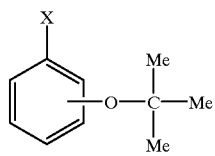

Wherein X represents a halogen atom.

Examples of the aromatic halogen compounds employable herein include benzene fluoride derivatives, chlorinated benzene derivatives, brominated benzene derivatives, and iodinated benzene derivatives.

As mentioned above, the production process of the present invention not only can give solution to the prior art problems and hence can produce a styrene derivative economically and safely on an industrial basis, but also enables a reaction which does not form biphenyl by-product at all.

The present invention will be further described in the following examples, but the present invention should not be construed as being limited thereto.

EXAMPLE 1

Into a 100 ml flask in which the air had been replaced by nitrogen were charged 10 ml of tetrahydrofuran, 1.34 g (55 mmol) of metallic magnesium and a piece of iodine, and the resulting mixture was stirred at room temperature. After confirmation of disappearance of the color of iodine, a solution of 11.46 g (50 mmol) of para-tertiary butoxybromobenzene dissolved in 20 ml of tetrahydrofuran was added dropwise to the reaction liquid over about 1 hour while maintaining the reaction solution at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction liquid was added 0.05 g (0.25 mmol) of manganese chloride tetrahydrate (II) ($MnCl_2.4H_2O$). 3.44g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by a gas chromatography to determine the yield of PTBS. The reaction results are shown in Table 1 below. Further, as a result of analyzing trace impurities with gas chromatography, biphenyl was not detected at all.

TABLE 1

| Example No. | Catalyst | Yield of PTBS (%) |
|---|---|---|
| Example 1 | $MnCl_2.4H_2O$ | 80.2 |
| Example 2 | $Mn(CH_3CO_2)_2.4H_2O$ | 81.1 |
| Example 3 | $MnBr_2$ | 80.6 |
| Example 4 | $MnCl_2$ (dppp) | 73.2 |
| Example 5 | $FeCl_3$ | 83.3 |
| Example 6 | $FeCl_2$ | 82.9 |
| Example 7 | $FeCl_2.4H_2O$ | 80.5 |
| Example 8 | $FeBr_2.4H_2O$ | 86.4 |
| Example 9 | $FeCl_2$ (dppp) | 86.2 |
| Example 10 | $FeCl_2$ $(PPh_3)_2$ | 83.1 |
| Example 11 | $FeCl_2$ (dpy) | 80.8 |
| Example 12 | $CoCl_2$ | 80.4 |
| Example 13 | $Co(CH_3CO_2)_2.4H_2O$ | 78.3 |
| Example 14 | $CoCl_2$ (dppp) | 77.8 |
| Example 15 | $RhCl_3.3H_2O$ | 79.9 |
| Example 16 | $MnCl_2.4H_2O + FeCl_3$ | 83.2 |
| Example 17 | $MnCl_2.4H_2O + CoCl_2$ | 80.0 |
| Example 18 | $FeCl_3 + CoCl_2$ | 81.4 |
| Comparative Example 1 | $NiCl_2$ (dppp) | 82.1 |
| Comparative Example 2 | $NiCl_2$ $(PPh_3)_2$ | 48.9 |
| Comparative Example 3 | $NiCl_2$ | 20.1 |
| Comparative Example 4 | $PdCl_2$ | 9.9 |

TABLE 1-continued

| Comparative Example 5 | CuCl$_2$ | 0.6 |
| Comparative Example 6 | AlCl$_3$ | 0.4 |

MnCl$_2$(dppp)

CoCl$_2$(dppp)

FeCl$_2$(dppp)

NiCl$_2$(dppp)

FeCl$_2$(dpy)

EXAMPLES 2 TO 15

Reaction was conducted in the same manner as in Example 1 except that the catalyst shown in Table 1 (0.25 mmol) was used instead of manganese chloride tetrahydrate (II) (0.25 mmol) The reaction results are shown in Table 1 above. Further, as a result of analyzing trace impurities with gas chromatography in Example 5, biphenyl was not detected al all.

EXAMPLE 16

Reaction was conducted in the same manner as in Example 1 that a mixture of 0.03 g (0.13 mmol) of manganese chloride tetrahydrate (II) and 0.02 g (0.13 mmol) of ferric chloride (III) was used instead of manganese chloride tetrahydrate (II) (0.25 mmol). The reaction results are shown in Table 1 above.

EXAMPLE 17

Reaction was conducted in the same manner as in Example 1 except that a mixture of 0.03 g (0.13 mmol) of manganese chloride tetrahydrate (II) and 0.02 g (0.13 mmol) of cobalt chloride (II) was used instead of manganese chloride tetrahydrate (II) (0.25 mmol). The reaction results are shown in Table 1 above.

EXAMPLE 18

Reaction was conducted in the same manner as in Example 1 except that a mixture of 0.02 g (0.13 mmol) of ferric chloride (III) and 0.02 g (0.13 mmol) of cobalt chloride (II) was used instead of manganese chloride tetrahydrate (II) (0.25 mmol) The reaction results are shown in Table 1 above.

COMPARATIVE EXAMPLE 1
(Use of catalyst described in JP 1-106835A and JP 2-160739A)

Reaction was conducted in the same manner as in Example 1 except that dichloro [1, 3-bis (diphenylphosphino) propane] nickel (0.25 mmol) was used in place of manganese chloride tetrahydrate (II) (0.25 mmol) used in Example 1. As a result, PTBS was formed in a yield of 82.1%. Further, as a result of analyzing trace impurities with gas chromatography, biphenyl was formed in an amount of 0.038%.

COMPARATIVE EXAMPLES 2 TO 6

Reaction was conducted in the same manner as in Example 1 except that the catalyst shown in Table 1 (0.25 mmol) was used instead of manganese chloride tetrahydrate (II) (0.25 mmol). The reaction results are shown in Table 1.

EXAMPLE 19

Into a 100 ml flask in which the air had been replaced by nitrogen were charged 10 ml of tetrahydrofuran, 1.34 g (55 mmol) of metallic magnesium and a piece of iodine. The resulting mixture was then stirred at room temperature. After the confirmation of disappearance of the color of iodine, a solution of 11.46 g (50 mmol) of meta-tertiary butoxybromobenzene dissolved in 20 ml of tetrahydrofuran was added dropwise to the reaction liquid over about 1 hour while maintaining the reaction liquid at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.06 g (0.25 mmol) of manganese acetate tetrahydrate (II) [Mn(CH$_3$CO$_2$)$_2$.4H$_2$O]. 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that MTBS had been produced in a yield of 81.8%.

EXAMPLE 20

Into a 100 ml flask in which the air had been replaced by nitrogen were charged 10 ml of diethyl ether, 1.34 g (55 mmol) of metallic magnesium and a piece of iodine. The resulting mixture was then stirred at room temperature. After the confirmation of disappearance of the color of iodine, a solution of 11.46 g (50 mmol) of meta-tertiary butoxybromobenzene dissolved in 20 ml of diethyl ether was added dropwise to the reaction liquid over about 1 hour while maintaining the reaction liquid at a temperature of 20 to 30° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.06 g (0.25 mmol) of manganese acetate tetrahydrate (II) [$Mn(CH_3CO_2)_2 \cdot 4H_2O$]. 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that MTBS had been produced in a yield of 71.3%.

EXAMPLE 21

Into a 100 ml flask in which the air had been replaced by nitrogen were charged 10 ml of dibutyl ether, 1.34 g (55 mmol) of metallic magnesium and a piece of iodine. The resulting mixture was then stirred at room temperature. After the confirmation of disappearance of the color of iodine, a solution of 11.46 g (50 mmol) of meta-tertiary butoxybromobenzene dissolved in 20 ml of dibutyl ether was added dropwise to the reaction liquid over about 1 hour while maintaining the reaction liquid at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.06 g (0.25 mmol) of manganese acetate tetrahydrate (II) [$Mn(CH_3CO_2)_2 \cdot 4H_2O$]. 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that MTBS had been produced in a yield of 68.9%.

EXAMPLE 22

Into a 100 ml flask in which the air had been replaced by nitrogen were charged 10 ml of tetrahydrofuran, 1.34 g (55 mmol) of metallic magnesium and a piece of iodine. The resulting mixture was then stirred at room temperature. After the confirmation of disappearance of the color of iodine, a solution of 11.46 g (50 mmol) of meta-tertiary butoxybromobenzene dissolved in 20 ml of tetrahydrofuran was added dropwise to the reaction liquid over about 1 hour while maintaining the reaction liquid at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.03 g (0.25 mmol) of cobalt chloride (II) ($CoCl_2$). 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that MTBS had been produced in a yield of 80.4%.

EXAMPLE 23

Into a 100 ml flask in which the air had been replaced by nitrogen were charged 10 ml of tetrahydrofuran, 2.68 g (110 mmol) of metallic magnesium and 0.65 g (6 mmol) of ethyl bromide. The resulting mixture was then stirred under reflux for 20 minutes. A solution of 18.47 g (100 mmol) of meta-tertiary butoxybromobenzene dissolved in 20 ml of tetrahydrofuran was added dropwise to the reaction liquid over about 2 hours under reflux. The reaction liquid was then stirred under reflux for 3 hours to obtain a Grignard reagent.

The supernatant liquid containing a Grignard reagent thus obtained was then transferred to a 100 ml flask in which the air had been replaced by nitrogen. Subsequently, to the reaction solution were added 0.13 g (1 mmol) of ferrous chloride (II) ($FeCl_2$) and 20 ml of tetrahydrofuran. 6.88 g (110 mmol) of vinyl chloride gas was then blown into the reaction liquid over 3 hours while maintaining the reaction temperature at 40 to 50° C. The reaction liquid was then stirred at the same temperature for 30 minutes.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that MTBS had been produced in a yield of 83.3%.

EXAMPLE 24

Into a 100 ml flask in which the air had been replaced by nitrogen were charged 10 ml of tetrahydrofuran, 2.68 g (110 mmol) of metallic magnesium and 0.65 g (6 mmol) of ethyl bromide. The resulting mixture was then stirred under reflux for 20 minutes. A solution of 18.47 g (100 mmol) of meta-tertiary butoxybromobenzene dissolved in 20 ml of tetrahydrofuran was added dropwise to the reaction liquid over about 2 hours under reflux. The reaction liquid was then stirred under reflux for 3 hours to obtain a Grignard reagent.

The supernatant liquid containing a Grignard reagent thus obtained was then transferred to a 100 ml flask in which the air had been replaced by nitrogen. Subsequently, to the reaction solution were added 0.13 g (1 mmol) of ferrous chloride (II) ($FeCl_2$) and 20 ml of toluene. 6.88 g (110 mmol) of vinyl chloride gas was then blown into the reaction liquid over 3 hours while maintaining the reaction temperature at 40 to 50° C. The reaction liquid was then stirred at the same temperature for 30 minutes.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that MTBS had been produced in a yield of 81.9%.

EXAMPLE 25

Into a 100 ml flask in which the air had been replaced by nitrogen were charged 10 ml of tetrahydrofuran, 1.34 g (55 mmol) of metallic magnesium and a piece of iodine. The resulting mixture was then stirred at room temperature. After th4e confirmation of disappearance of the color of iodine, a solution of 8.55 g (50 mmol) of para-bromotoluene dissolved in 20 ml of tetrahydrofuran was added dropwise to the reaction liquid over about 1 hour while maintaining the reaction liquid at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.05 g (0.25 mmol) of manganese chloride tetrahydrate (II) ($MnCl_2.4H_2O$). 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-methylstyrene had been produced in a yield of 64.1%.

EXAMPLE 26

Into a 100 ml flask in which the air had been replaced by nitrogen were charged 10 ml of tetrahydrofuran, 1.34 g (55 mmol) of metallic magnesium and a piece of iodine. The resulting mixture was then stirred at room temperature. After the confirmation of disappearance of the color of iodine, a solution of 8.55 g (50 mmol) of para-bromotoluene dissolved in 20 ml of tetrahydrofuran was added dropwise to the reaction liquid over about 1 hour while maintaining the reaction solution at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.03 g (0.25 mmol) of cobalt chloride (II) ($CoCl_2$). 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-methylstyrene had been produced in a yield of 64.3%.

EXAMPLE 27

Into a 100 ml flask in which the air had been replaced by nitrogen were charged 10 ml of tetrahydrofuran, 2.68 g (110 mmol) of metallic magnesium and 0.65 g (8 mmol) of ethyl bromide. The resulting mixture was then stirred under reflux for 20 minutes. A solution of 12.66 g (100 mmol) of para-chlorotoluene dissolved in 20 ml of tetrahydrofuran was added to the reaction liquid over about 2 hours under reflux.

The reaction solution was then stirred under reflux for 3 hours to obtain a Grignard reagent.

The supernatant liquid containing a Grignard reagent thus obtained was then transferred to a 100 ml flask in which the air had been replaced by nitrogen. Subsequently, to the reaction solution were added 0.13 g (1 mmol) of ferrous chloride (II) ($FeCl_2$) and 20 ml of tetrahydrofuran. 6.88 g (110 mmol) of vinyl chloride gas was then blown into the reaction liquid over about 3 hours while maintaining the reaction temperature at 40 to 50° C. The reaction liquid was then stirred at the same temperature for 30 minutes.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-methylstyrene had been produced in a yield of 64.3%.

EXAMPLE 28

Into a 100 ml flask in which the air had been replaced by nitrogen were charged 10 ml of tetrahydrofuran, 1.34 g (55 mmol) of metallic magnesium and a piece of iodine. The resulting mixture was then stirred at room temperature. After the confirmation of disappearance of the color of iodine, a solution of 9.57 g (50 mmol) of para-bromochlorobenzene dissolved in 20 ml of tetrahydrofuran was added dropwise to the reaction liquid over about 1 hour while maintaining the reaction solution at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.06 g (0.25 mmol) of manganese acetate tetrahydrate (II) [$Mn(CH_3CO_2)_2.4H_2O$]. 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-chlorostyrene had been produced in a yield of 60.7%.

EXAMPLE 29

Into a 100 ml flask in which the air had been replaced by nitrogen were charged 10 ml of tetrahydrofuran, 1.34 g (55 mmol) of metallic magnesium and a piece of iodine. The resulting mixture was then stirred at room temperature. After the confirmation of disappearance of the color of iodine, a solution of 9.57 g (50 mmol) of para-bromochlorobenzene dissolved in 20 ml of tetrahydrofuran was added dropwise to the reaction liquid over about 1 hour while maintaining the reaction liquid at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.03 g (0.25 mmol) of cobalt chloride (II) ($CoCl_2$). 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-chlorostyrene had been produced in a yield of 67.1%.

EXAMPLE 30

Into a 100 ml flask in which the air had been replaced by nitrogen were charged 10 ml of dibutyl ether, 1.34 g (55 mmol) of metallic magnesium and a piece of iodine. The resulting mixture was then stirred at room temperature. After the confirmation of disappearance of the color of iodine, a solution of 9.57 g (50 mmol) of para-bromochlorobenzene dissolved in 20 ml of dibutyl ether was added dropwise to the reaction liquid over about 1 hour while maintaining the reaction solution at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.03 g (0.25 mmol) of cobalt chloride (II) ($CoCl_2$). 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-chlorostyrene had been produced in a yield of 55.4%.

EXAMPLE 31

Into a 100 ml flask in which the air had been replaced by nitrogen were charged 10 ml of tetrahydrofuran, 1.34 g (55 mmol) of metallic magnesium and a piece of iodine. The resulting mixture was then stirred at room temperature. After the confirmation of disappearance of the color of iodine, a solution of 9.57 g (50 mmol) of para-bromochlorobenzene dissolved in 20 ml of tetrahydrofuran was added dropwise to the reaction liquid over about 1 hour while maintaining the reaction solution at a temperature of 40 to 50° C. The reaction liquid was then stirred under reflux for 1 hour to obtain a Grignard reagent.

The supernatant liquid containing a Grignard reagent thus obtained was then transferred to a 100 ml flask in which the air had been replaced by nitrogen. Subsequently, to the reaction solution was added 0.07 g (0.25 mmol) of rhodium chloride trihydrate (III) ($RhCl_3.3H_2O$). 3.44 g (55 mmol) of vinyl chloride gas was then blown into the reaction liquid over 10 minutes while maintaining the reaction temperature at 20 to 30° C. The reaction liquid was then stirred at the same temperature for 1 hour.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-chlorostyrene had been produced in a yield of 64.8%.

EXAMPLE 32

Into a 100 ml flask in which the air had been replaced by nitrogen were charged 10 ml of tetrahydrofuran, 2.68 g (110 mmol) of metallic magnesium and 0.65 g (8 mmol) ethyl bromide. The resulting mixture was then stirred under reflux for 20 minutes. Subsequently, a solution of 12.66 g (100 mmol) of para-dichlorobenzene dissolved in 20 ml of tetrahydrofuran was added dropwise to the reaction liquid over about 2 hours under reflux. The reaction liquid was then stirred under reflux for 3 hours to obtain a Grignard reagent.

The supernatant liquid containing a Grignard reagent thus obtained was then transferred to a 100 ml flask in which the air had been replaced by nitrogen. Subsequently, to the reaction solution were added 0.08 g (0.5 mmol) of ferric chloride ($FeCl_3$) and 30 ml of toluene. 10.46 g (167 mmol) of vinyl chloride gas was then blown into the reaction liquid over about 3 hours while maintaining the reaction temperature at 40 to 50° C. The reaction liquid was then stirred at the same temperature for 30 minutes.

After completion of the reaction, an aqueous solution of ammonium chloride was added to the reaction liquid to dissolve the salt thus produced therein. The resulting organic phase was dispensed, and then analyzed by gas chromatography. As a result, it was confirmed that para-chlorostyrene had been produced in a yield of 62.9%.

EXAMPLE 33

Into a 50 liters flask in which the air had been replaced by nitrogen were charged 6 l of tetrahydrofuran, 0.73 kg (30 mol) of metallic magnesium and 0.22 kg (2 mol) ethyl bromide. The resulting mixture was then stirred under reflux for 1 hour. Subsequently, a solution of 4.62 kg (25 mol) of para-tertiary butoxychlorobenzene dissolved in 5 liters of tetrahydrofuran was added dropwise to the reaction liquid over about 2 hours under reflux. The reaction liquid was then stirred under reflux for 4 hours to obtain a Grignard reagent.

The supernatant liquid containing a Grignard reagent thus obtained was then cooled to a temperature of 40° C. To the reaction solution were then added 0.02 kg (0.12 mol) of ferric chloride (III) (FeCl3) and 12 liters of tetrahydrofuran. 1.88 kg (30 mol) of vinyl chloride gas was then blown into the reaction liquid over about 7 hours while maintaining the reaction temperature at 40 to 50° C. The reaction liquid was then stirred at the same temperature for 1 hour.

After completion the reaction, an aqueous solution of ammonium chloride was added to the reaction liquid to dissolve the salt thus produced therein. The resulting organic phase was then separated. The organic phase thus obtained was washed with saturated brine, and then subjected to distillation to remove the solvent therefrom. To the residue was then added a polymerization inhibitor. The residue was then distilled under reduced pressure to obtain a PTBS fraction having a boiling point of 92° C./5 mmHg in a yield of 3.58 kg (81.2%).

While the invention has been described in detail and with reference to specific embodiments thereof, it will be apparent to one skilled in the art that various changes and modifications can be made therein without departing from the spirit and scope thereof.

What is claimed is:
1. A process for the production of a styrene compound which comprises reacting a Grignard reagent prepared from a tertiary butoxyphenyl halide represented by the following formula (I):

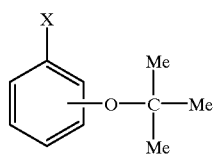

wherein X represents a halogen atom, with a vinyl halide in the presence of a catalyst, wherein said catalyst is at least one member selected from the group consisting of a manganese catalyst, an iron catalyst, a cobalt catalyst and a rhodium catalyst.

2. The process for the production of a styrene compound as claimed in claim 1, wherein said catalyst is a manganese catalyst.

3. The process for the production of a styrene compound as claimed in claim 1, wherein said catalyst is an iron catalyst.

4. The process for the production of a styrene compound as claimed in claim 3, wherein said iron catalyst comprises ferrous halide and/or ferric halide.

5. The process for the production of a styrene compound as claimed in claim 3, wherein said iron catalyst comprises a catalyst prepared from ferrous halide and/or a catalyst prepared from ferric halide.

6. The process for the production of a styrene compound as claimed in claim 1, wherein said catalyst is a cobalt catalyst and/or a rhodium catalyst.

7. The process for the production of a styrene compound as claimed in claim 1, wherein said tertiary butoxyphenyl halide is a para-tertiary butoxyphenyl halide.

8. The process for the production of a styrene compound as claimed in claim 1, wherein said reaction is conducted in tetrahydrofuran or a mixed solvent containing tetrahydrofuran.

9. A process for the production of a styrene compound which comprises reacting a Grignard reagent prepared from an aromatic halogen compound with a vinyl halide in the presence of a catalyst, wherein said catalyst is at least one member selected from the group consisting of a manganese catalyst and a rhodium catalyst.

10. The process for the production of a styrene compound as claimed in claim 9, wherein said catalyst is a manganese catalyst.

11. The process for die production of a styrene compound as claimed in claim 9, wherein said catalyst is a rhodium catalyst.

12. The process for the production of a styrene compound as claimed in claim 9, wherein said aromatic halogen compound is a tertiary butoxyphenyl halide represented by the following formula (I):

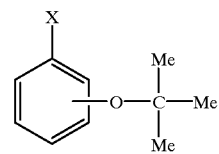

wherein X represents a halogen atom.

13. The process for the production of a styrene derivative as claimed in claim 12, wherein said tertiary butoxyphenyl halide is a para-tertiary butoxyphenyl halide.

14. The process for the production of a styrene derivative as claimed in claim 12, wherein said reaction is conducted in tetrahydrofuran or a mixed solvent containing tetrahydrofuran.

* * * * *